US012723018B2

(12) United States Patent
Wang et al.

(10) Patent No.: US 12,723,018 B2

(45) Date of Patent: Sep. 1, 2026

(54) CINNAMOYL AMINO ACID COMPOUND AND USE THEREOF

(71) Applicant: CHINA PHARMACEUTICAL UNIVERSITY, Nanjing (CN)

(72) Inventors: Hao Wang, Nanjing (CN); Xiaolong Hu, Nanjing (CN); Xianyu Lv, Nanjing (CN); Fei Xiong, Nanjing (CN); Jiahao Feng, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 719 days.

(21) Appl. No.: 17/913,776

(22) PCT Filed: Aug. 5, 2020

(86) PCT No.: PCT/CN2020/107122

§ 371 (c)(1),
(2) Date: Sep. 22, 2022

(87) PCT Pub. No.: WO2021/189750

PCT Pub. Date: Sep. 30, 2021

(65) Prior Publication Data

US 2024/0217921 A1 Jul. 4, 2024

(30) Foreign Application Priority Data

Mar. 24, 2020 (CN) ......................... 202010213184.5

(51) Int. Cl.

| | |
|---|---|
| ***C07C 233/51*** | (2006.01) |
| ***A61K 31/192*** | (2006.01) |
| ***A61P 9/10*** | (2006.01) |
| ***A61P 25/16*** | (2006.01) |

(52) U.S. Cl.

CPC .......... *C07C 233/51* (2013.01); *A61K 31/192* (2013.01); *A61P 9/10* (2018.01); *A61P 25/16* (2018.01)

(58) Field of Classification Search

CPC ........ C07C 233/511; A61P 9/10; A61P 25/16; A61K 9/0014; A61K 31/192

See application file for complete search history.

(56) References Cited

FOREIGN PATENT DOCUMENTS

| | | |
|---|---|---|
| CN | 102405079 A | 4/2012 |
| CN | 108484431 A | 9/2018 |

OTHER PUBLICATIONS

Park et al., “Synthesis of Clovamide Analogues That Inhibit NO Production in Activated BV-2 Microglial Cells,” Biol. Phar. Bull. 40, 1475-1482 (2017). (Year: 2017).*

Hu et al., “Synthesis and biological evaluation of clovamide analogues as potent anti-neuroinflammatory agents in vitro and in vivo,” European Journal of Medicinal Chemistry 151 (2018) 261-271. (Year: 2018).*

Xiao-Long et al., “Optimization of N Phenylpropenoyl L amino Acids as Potent and Selective Inducible Nitric Oxide Synthase Inhibitors for Parkinson’s Disease,” J. Med. Chem. 2021, 64, 7760-7777. (Year: 2021).*

Nov. 27, 2020 International Search Report issued in International Patent Application No. PCT/CN2020/107122.

Sep. 22, 2022 International Preliminary Report on Patentability issued in International Patent Application No. PCT/CN2020/107122.

Jun Lin et al.; “Research Progress in N-Phenylpropenoyl-L-amino Acids”; Progress in Pharmaceutical Sciences; 2018; vol. 42; No. 1; pp. 52-59.

* cited by examiner

*Primary Examiner* — Jared Barsky

(74) *Attorney, Agent, or Firm* — Oliff PLC

(57) ABSTRACT

Cinnamoyl amino acid compounds and a use thereof, which relate to the fields of medicinal chemistry and pharmacotherapeutics, and specifically relate to cinnamoyl amino acid compounds having inducible nitric oxide synthase (iNOS) inhibitory activity or a pharmaceutically acceptable salt thereof, a pharmaceutical composition including the compounds, and a medical use thereof, particularly an application thereof in the prevention and treatment of neurodegenerative diseases related to nerve cell damage, including ischemic stroke, Parkinson’s disease, and so on.

2 Claims, 2 Drawing Sheets

CINNAMOYL AMINO ACID COMPOUND AND USE THEREOF

TECHNICAL FIELD

The present disclosure relates to a cinnamoyl amino acid compound, and in particular to a cinnamoyl amino acid compound having inducible nitric oxide synthase (iNOS) inhibitory activity, and application thereof in drugs for prevention and treatment of ischemic stroke and Parkinson's disease, belonging to the technical field of pharmacy.

BACKGROUND

Apoplexy, also known as stroke, refers to acute cerebral blood circulation disorder caused by intracerebral arterial stenosis, occlusion or rupture in patients with cerebrovascular diseases due to various predisposing factors, and can be divided into hemorrhagic stroke and ischemic stroke. Ischemic stroke accounts for about 70% of the total incidence of stroke, and has become one of the three major causes of death in developed countries. Worldwide, there are about 15 million ischemic stroke patients every year, of whom about ⅓ die and ⅓ are permanently disabled, causing serious social and economical burdens. Up to now, recombinant tissue plasminogen activator (rt-PA) is the only drug approved by FDA for acute ischemic stroke treatment, but rt-PA has a limited 4.5-h treatment time window and potential risk of hemorrhagic transformation. Therefore, there is an urgent need for a new effective therapeutic strategy for ischemic stroke.

Parkinson's disease (PD) is a chronic degenerative disease of the motor system, which is mainly caused by progressive or selective degeneration of nigrostriatal dopaminergic nerves. It is generally believed that advanced age or genetic predisposition is the main cause of PD in patients. Modern clinical studies have shown that neuroinflammation plays an important role in the development of PD. Based on relevant medical experiments, medical researchers have found that neuroinflammation can not only induce the occurrence of PD, but also aggravate the development of PD. Microglia and peripherally invading T lymphocytes in neuroinflammation can lead to the occurrence of PD and aggravate the development of the disease. At present, there is no drug that can effectively treat Parkinson's disease clinically, and the development of drugs for Parkinson's disease prevention and treatment is also very important.

Inflammatory response plays an important role in the pathological process of ischemia-induced brain injury. One of the important markers of inflammatory response after cerebral ischemia or Parkinson's disease is the activation of glial cells. Glial cells, as the most abundant immune cells in the central nervous system, can not only provide nutrition and support for neurons, but also regulate the release of neurotransmitters and maintain the balance of brain homeostasis, and thus play an extremely important role in neurological diseases. When being activated massively, glial cells will also secrete a large number of inflammatory factors and neurotoxic substances, triggering the inflammatory response. It is found that the expression of glial fibrillary acidic protein, a marker of astrocyte activation, is significantly increased in the brains of rats with focal cerebral ischemic injury. In addition, a large number of activated microglial cells can be seen in the brains of patients with ischemic stroke or Parkinson's disease, indicating that microglial cells are closely related to the pathogenesis of cerebral ischemia and Parkinson's disease. Therefore, inhibiting the over-activation of microglial cells to block the inflammatory response mediated by microglial cells is an effective means to prevent and treat cranial nerve injury diseases such as ischemic stroke or Parkinson's disease.

Inducible nitric oxide synthase (iNOS), which is generally in a silent state in living organisms, is induced and activated by inflammatory cytokines or endotoxins, and can synthesize NO in large amount after generation. Excessive NO causes DNA damage, mitochondrial respiratory depression, and the like. More seriously, it forms reactive nitrogen such as peroxynitrite anion ($ONOO^-$) with superoxide anion ($O^{2-}$), performs nitriding-modification on key proteins, and changes the signal pathway, directly and indirectly mediating the cytotoxic effect of NO. In addition, multiple cascade signals are activated, and these signaling pathways affect each other to form an inflammatory cascade reaction, promoting the development of inflammation, and leading to a variety of diseases, such as ischemic stroke and Parkinson's disease as mentioned above.

Ferulic acid, with chemical name of 4-hydroxy-3-methoxycinnamic acid, is a derivative of cinnamic acid (chemical name: cinnamylic acid). According to reports in the literature, ferulic acid and its sodium salts have neuroprotective effects, and sodium ferulate has a protective effect on nerve oxidative damage caused by chronic cerebral ischemia. Sodium ferulate can reduce the excitotoxicity of nerve cells produced by glutamic acid, and the size of cerebral infarction, and has obvious therapeutic effect of reducing focal cerebral ischemia injury. The neuroprotective mechanism above is closely related to the anti-neuroinflammatory effect of ferulic acid. However, it is difficult for ferulic acid and its sodium salts to pass through the blood-brain barrier due to poor lipophilicity, and ferulic acid and its sodium salts have the problems of low bioavailability, and short in vivo duration of effective drug concentration, which severely limits the clinical application of sodium ferulate as a neuroprotective drug. As a ferulic acid analog, cinnamic acid has strong lipophilicity and can easily pass through the blood-brain barrier. In this study, cinnamic acid is used as a lead compound for structural modification to discover a neuroinflammation protective drug with druggability. In the previous research of this subject, 26 cinnamoyl amino acid derivatives are designed and synthesized, and the structure-activity relationship of iNOS inhibitory activity is studied. It is found that 4-hydroxy-3-methoxycinnamoyl-L-tyrosine has the strongest iNOS inhibitory effect. A rat ischemia-reperfusion model (MCAO model) and an MPTP-induced mouse Parkinson's disease model show that it has good anti-cerebral ischemia and anti-Parkinson's disease effects (see patent CN108484431A for details). Subsequently, in order to further improve the activity and druggability of the compound, in follow-up studies, structural modification and optimization are carried out, and a newly structured compound with stronger iNOS inhibitory activity, i.e., the compound of this application 4-trifluoromethyl-cinnamoyl-4-fluoro-L-phenylalanine are unexpectedly obtained.

SUMMARY

Objective of the present disclosure: In view of the prior art above, the present disclosure provides a cinnamoyl amino acid compound having inducible nitric oxide synthase (iNOS) inhibitory activity, and a medical use thereof.

Technical solution: A 4-trifluoromethyl-cinnamoyl-4-fluoro-L-phenylalanine according to this application is a compound shown in structural formula I or an optical isomer, enantiomer, diastereomer, racemate or racemic mixture thereof, or a pharmaceutically acceptable salt thereof:

formula I

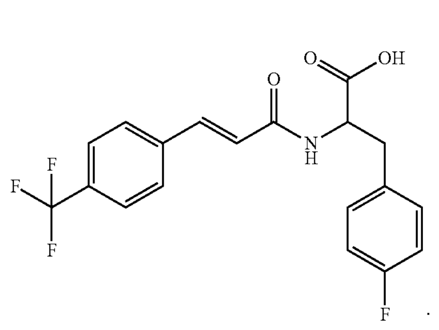

In another aspect, the present disclosure provides an application of the above 4-trifluoromethyl-cinnamoyl-4-fluoro-L-phenylalanine in preparation of a drug for prevention and treatment of neurodegenerative diseases related to nerve cell damage. The neurodegenerative diseases include ischemic stroke, Parkinson's disease and the like. Preferably, the drug is taken orally or injected.

In another aspect, the present disclosure provides a pharmaceutical composition, including a therapeutically effective amount of one or more of the above 4-trifluoromethyl-cinnamoyl-4-fluoro-L-phenylalanines and/or a pharmaceutically acceptable salt thereof.

The present disclosure also claims an application of the pharmaceutical composition in preparation of a drug for prevention and treatment of neurodegenerative diseases related to nerve cell damage. The neurodegenerative diseases include ischemic stroke, Parkinson's disease and the like.

Based on a large number of medicinal chemistry and pharmacological scientific experiments, the present disclosure proves that the cinnamoyl amino acid compounds have significant anti-neuroinflammatory effects and can effectively inhibit iNOS activity. Further, for the optimal compound 4-trifluoromethyl-cinnamoyl-4-fluoro-L-phenylalanine, the in vivo effect of anti-ischemic stroke and anti-Parkinson's disease is studied. The results show that oral administration of 4-trifluoromethyl-cinnamoyl-4-fluoro-L-phenylalanine (1 mg/kg, or 2 mg/kg) has a significant treatment effect on ischemic stroke and Parkinson's disease, which is obviously better than that of listed drugs. The compound has high blood-brain barrier permeability, good pharmacokinetic parameters, less toxic and side effects, and high safety, providing a new drug with high efficiency and low toxicity for patients with ischemic stroke and Parkinson's disease.

Beneficial effects: In order to further improve the anti-neuroinflammatory activity and blood-brain barrier permeability of cinnamoyl amino acid derivatives, the present disclosure designs and synthesizes 20 cinnamoyl amino acid compounds and carries out iNOS enzyme activity test. The results show that 4-trifluoromethyl-cinnamoyl-4-fluoro-L-phenylalanine has a strong iNOS inhibitory effect, and is the most effective iNOS inhibitor so far. In an in vivo model of cerebral ischemia reperfusion-induced cerebral ischemia, 4-trifluoromethyl-cinnamoyl-4-fluoro-L-phenylalanine shows stronger anti-cerebral ischemia activity than a positive drug butylphthalide, and 4-hydroxy-3-methoxycinnamoyl-L-tyrosine. In an in vivo model of MPTP-induced mouse Parkinson's disease, the effect of 4-trifluoromethyl-cinnamoyl-4-fluoro-L-phenylalanine in the prevention and treatment of Parkinson's disease is obviously better than that of a positive drug levodopa and 4-hydroxy-3-methoxycinnamoyl-L-tyrosine. The compound 4-trifluoromethyl-cinnamoyl-4-fluoro-L-phenylalanine of the present disclosure, and the pharmaceutical composition containing the compound have important medicinal prospects in the prevention and treatment of diseases related to neuroinflammation, including ischemic stroke, Parkinson's disease, and the like.

DETAILED DESCRIPTION

Figure 1:
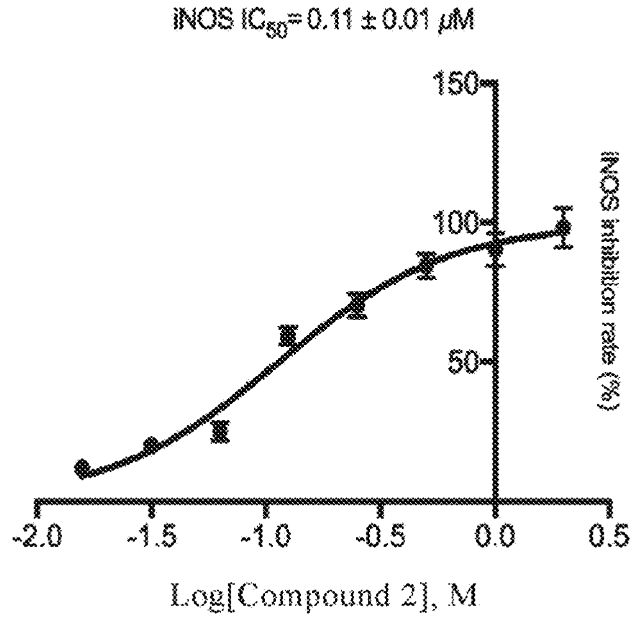
FIG. 1 shows an $IC_{50}$ result of an iNOS inhibition rate of a compound 4-trifluoromethyl-cinnamoyl-4-fluoro-L-phenylalanine of this application.

This application will be further described below in conjunction with the specific examples.

For the preparation of 4-hydroxy-3-methoxycinnamoyl-L-tyrosine, reference may be made to: Hu, X. L., Lin, J., Lv, X. Y., Feng, J. H., Zhang, X. Q., Wang, H., Ye, W. C., 2018. Synthesis and biological evaluation of clovamide analogues as potent anti-neuroinflammatory agents in vitro and in vivo. European Journal of Medicinal Chemistry 151, 261-271.

EXAMPLE 1

Synthesis of Compound 4-trifluoromethyl-cinnamoyl-4-fluoro-L-phenylalanine of the Present Disclosure Experimental reagents: Thionyl chloride, methanol, ethanol, potassium carbonate and dipotassium phosphate purchased from Sinopharm Chemical Reagent Co., Ltd .; 4-(4, 6-dimethoxy-triazin-2-yl)-4-methyl morpholinium chloride (DMTMM) purchased from Macklin Biological Company; and 4-fluoro-L-phenylalanine and 4-trifluoromethylcinnamic acid purchased from Adamas Reagent Company.

The synthetic route was as follows:

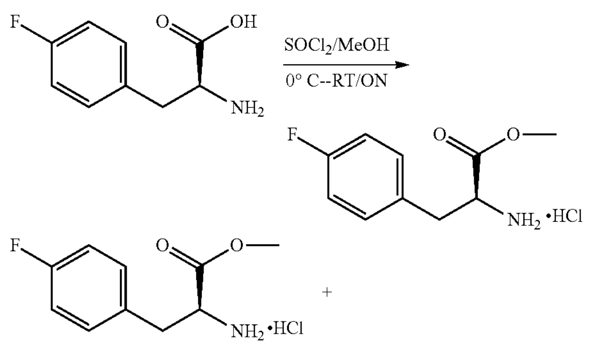

-continued

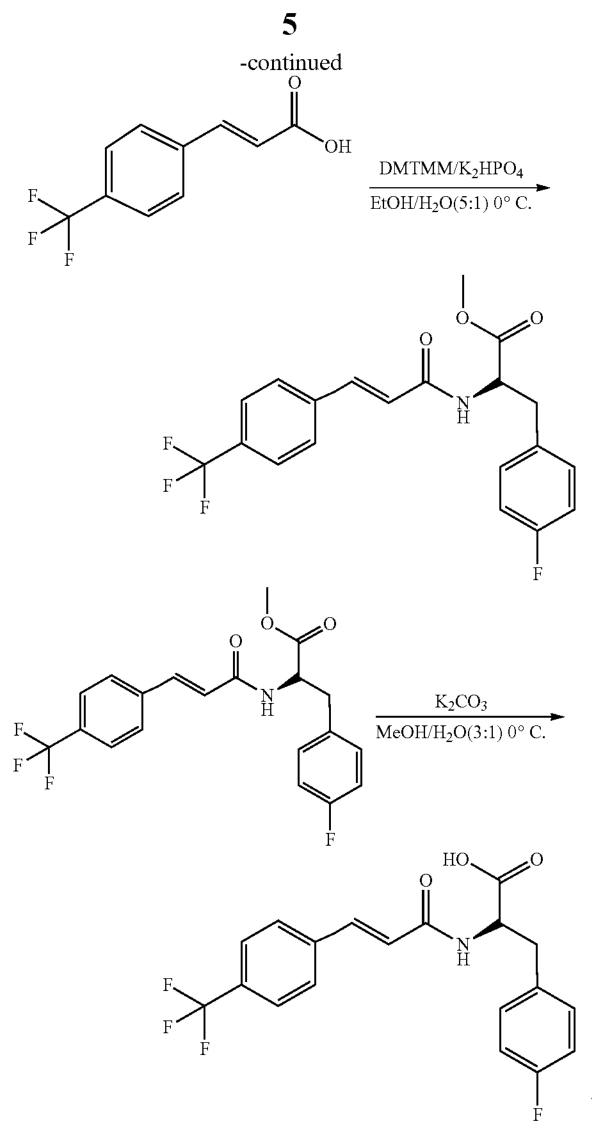

Experimental process: The amino acid methyl ester hydrochloride was prepared from a thionyl chloride/methanol system first, and a condensing agent DMTMM, which is resistant to protic solvents, was selected, and amide condensation was completed in aqueous ethanol. Finally, the methyl ester of the amino acid part is removed by a methanol/water/potassium carbonate system to expose the carboxyl group to obtain the target compound 4-trifluoromethyl-cinnamoyl-4-fluoro-L-phenylalanine.

Physicochemical properties: White amorphous powder (yield 61%), easily soluble in methanol, acetone, ethyl acetate, soluble in dichloromethane, insoluble in petroleum ether, water, dark spots at UV 254 nm, melting point 236-238° C., $[\alpha]^{20}$=11.2, ESI-MS m/z:$[M-H]^-$ 380, $[2M-H]^-$ 761, molecular formula: $C_{19}H_{15}F_4NO_3$ Spectral data: $^1$H-NMR (300 MHz, DMSO-$d_6$) $\delta_H$: 12.79 (1H, s), 8.51 (1H, d, J=8.1 Hz), 7.77 (4H, s), 7.47 (1H, d, J=15.9 Hz), 7.28 (2H, m), 6.84 (1H, d, J=15.9 Hz), 4.58 (1H, m), 3.14 (1H, dd, J=13.9 Hz, 4.9 Hz), 2.94 (1H, dd, J=13.9 Hz, 9.3 Hz) $^{13}$C-NMR (75 MHz, DMSO-$d_6$) $\delta_C$:175.78, 167.45, 165.72, 162.52, 141.92, 140.63, 136.69, 134.03, 133.92, 132.55, 131.25 (2C), 128.86 (2C), 127.50 (2C), 118.10, 117.82, 56.72, 39.05

EXAMPLE 2

In Vitro iNOS Inhibitory Effect of Compound 4-trifluoromethyl-cinnamoyl-4-fluoro-L-phenylalanine of the Present Disclosure Experimental materials: BV-2 cells (purchased from Shanghai Cell Bank, Chinese Academy of Sciences), DMEM cell culture fluid (Sigma), fetal bovine serum (Gibico), 96-well cell culture plate (Corning), DMSO (Sigma), LPS (Sigma), iNOS activity detection kit (Beyotime), test drug 4-trifluoromethyl-cinnamoyl-4-fluoro-L-phenylalanine prepared in Example 1, and microplate reader.

Experimental method: The BV-2 cells were seeded in the 96-well plate at a density of $1\times10^4$ cells/well, and a blank group, an LPS model group, and an LPS+compound 4-trifluoromethyl-cinnamoyl-4-fluoro-L-phenylalanine (0.01-10 μM) group were set and cultured for 24 hours. Then according to the group, the drug or blank culture fluid was added to the corresponding group for culture for 4 hours. Finally, except the blank group, each group was stimulated with LPS with a final concentration of 500 ng/mL for 24 hours. The iNOS activity assay was performed according to the requirements of the iNOS detection kit.

Results and discussion: As shown in FIG. 1, the compound 4-trifluoromethyl-cinnamoyl-4-fluoro-L-phenylalanine of this application (Compound 2 shown) has a very strong iNOS inhibitory effect, with an $IC_{50}$ value of 110 nM, and is the compound with the strongest iNOS inhibitory activity among natural products or synthetic compounds by far.

EXAMPLE 3

In Vivo Anti-Parkinsonian Activity of Compound 4-trifluoromethyl-cinnamoyl-4-fluoro-L-phenylalanine of the Present Disclosure Experimental materials: 10-week-old C57BL/6 male mice (Nanjing Qinglongshan Farm), rota-rod treadmill (Beijing Zhongshi Technology), levodopa and MPTP (Sigma), test drug 4-trifluoromethyl-cinnamoyl-4-fluoro-L-phenylalanine prepared in Example 1 (Compound 2 shown), and test drug 4-hydroxy-3-methoxycinnamoyl-L-tyrosine (Compound 1 shown).

Experimental groups: Mice were randomly divided into 5 groups, 10 mice in each group: a blank group, a model group, a 4-hydroxy-3-methoxycinnamoyl-L-tyrosine (Compound 1 shown, 2 mg/kg) group, a 4-trifluoromethyl-cinnamoyl-4-fluoro-L-phenylalanine (Compound 2 shown, 2 mg/kg) group and a levodopa (15 mg/kg) group. Pre-dosing by gavage was carried out for 12 consecutive days. The blank group and the model group were given equal doses of PBS, and modeling was performed on the $13^{th}$ day. The model group and the drug group were intraperitoneally injected with MPTP (20 mg/kg), once every 2 h, for 4 consecutive injections. After modeling, behavioral tests were carried out. The behavioral performance of mice was tested with a YLS-4C mouse rota-rod treadmill at 4 h, 24 h, 48 h, and 72 h after MPTP modeling. The time from the start of rotation of the rota-rod to the time leaving the rota-rod of the test mice was taken as the latency. The test time was 180 s, and each mouse was tested 3 times to obtain an average value. Training was carried out for 3 consecutive days before the test, twice a day.

Figure 2:
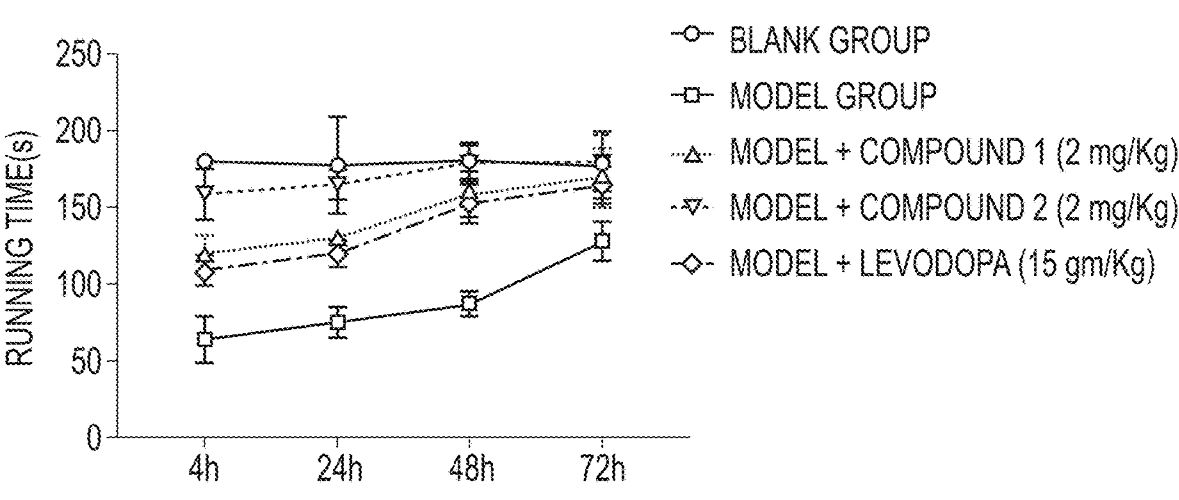
FIG. 2 shows anti-Parkinsonian effect results of the compound 4-trifluoromethyl-cinnamoyl-4-fluoro-L-phenylalanine of this application, a compound 4-hydroxy-3-methoxycinnamoyl-L-tyrosine and a positive drug levodopa.

Results and Discussion: FIG. 2 shows the Parkinsonian mouse rota-rod experiment. The compound 4-trifluoromethyl-cinnamoyl-4-fluoro-L-phenylalanine of this application (Compound 2 shown) can effectively alleviate the dyskinesia of the Parkinsonian mice at a lower dose (2 mg/kg), and increase the running time of the Parkinsonian mice. The effect is obviously better than that of the compound 4-hydroxy-3-methoxycinnamoyl-L-tyrosine (Compound 1 shown) and the listed drug levodopa. The experimental result shows that the compound 4-trifluoromethyl-cinnamoyl-4-fluoro-L-phenylalanine of this application (Compound 2 shown) can be used for preparing a drug for treatment and prevention of Parkinson's disease.

EXAMPLE 4

In Vivo Anti-Ischemic Brain Injury Activity of Compound 4-trifluoromethyl-cinnamoyl-4-fluoro-L-phenylalanine of the Present Disclosure (Compound 2 Shown)

Experimental materials: Male SD rats, weighing 250-300 g, provided by the Model Animal Research Center of Nanjing University and raised in the Experimental Animal Center of China Pharmaceutical University; triphenyl tetrazolium chloride (TTC) and butyphthalide purchased from Sigma; test drug 4-trifluoromethyl-cinnamoyl-4-fluoro-L-phenylalanine prepared in Example 1 (Compound 2 shown), and test drug 4-hydroxy-3-methoxycinnamoyl-L-tyrosine (Compound 1 shown).

Experimental method: The rats were randomly divided into 5 groups, i.e., a blank group, a model group (MCAO group), an MCAO+4-hydroxy-3-methoxycinnamoyl-L-tyrosine (Compound 1 shown, 2 mg/kg) group, an MCAO+4-trifluoromethyl-cinnamoyl-4-fluoro-L-phenylalanine (Compound 2 shown, 2 mg/kg) group and an MCAO+positive drug butyphthalide (5 mg/kg) group. After successful modeling, administration of different doses of compounds by gavage was carried out every day for 15 consecutive days. After the administration, brains were harvested, subjected to TTC staining, and photographed and recorded.

Figure 3:
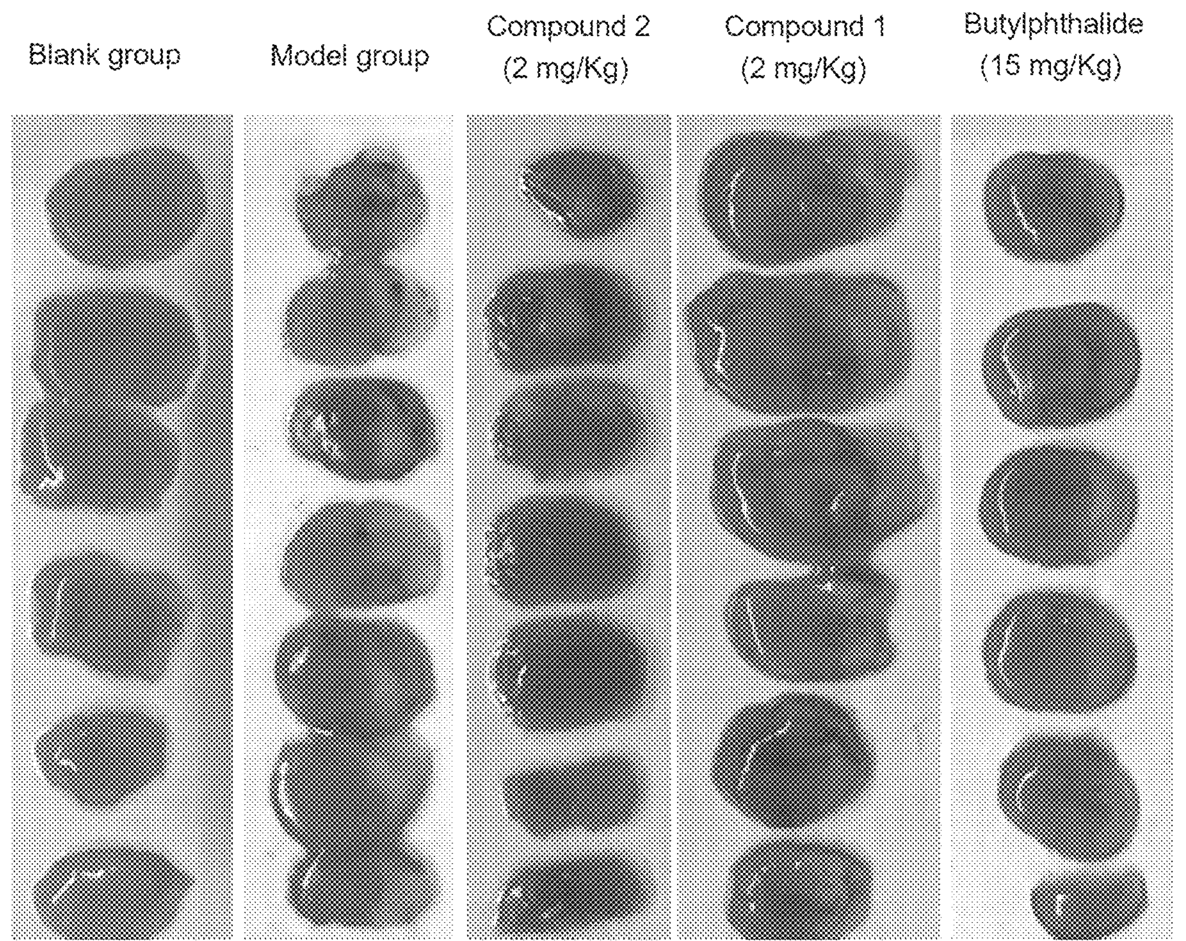
FIG. 3 shows effects of the compound 4-trifluoromethyl-cinnamoyl-4-fluoro-L-phenylalanine of this application, the compound 4-hydroxy-3-methoxycinnamoyl-L-tyrosine and a positive drug butyphthalide on the size of cerebral ischemia-induced cerebral infarction.

Experimental result: As shown in FIG. 3, the rat ischemia-reperfusion in-vivo model was used in combination with the TTC staining method to verify the effect of the test compounds on the size of cerebral infarction after 24 hours of ischemia reperfusion in rats. The experimental result shows that: 4-trifluoromethyl-cinnamoyl-4-fluoro-L-phenylalanine (Compound 2 shown) can effectively reduce the increase in the size of cerebral infarction caused by ischemia reperfusion at a very low dose (2 mg/kg). The effect is better than that of the positive drug and 4-hydroxy-3-methoxycinnamoyl-L-tyrosine (Compound 1 shown). On the one hand, this result confirms the in vivo effectiveness of the compound 4-trifluoromethyl-cinnamoyl-4-fluoro-L-phenylalanine of this application, and on the other hand, it can also indirectly verify the in vitro experimental result.

What is claimed is:

1. A method of treating a neurodegenerative disease in a subject in need thereof wherein said method comprises administering a composition comprising:

4-trifluoromethyl-cinnamoyl-4-fluoro-L-phenylalanine, being shown in structural formula I or a pharmaceutically acceptable salt thereof drug:

formula I

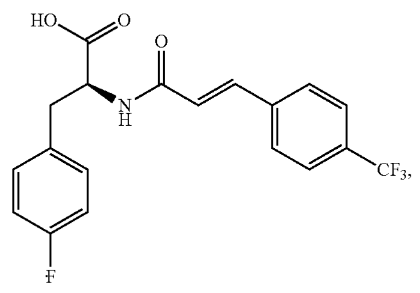

and the neurodegenerative disease is related to nerve cell damage and is ischemic stroke or Parkinson's disease.

2. The method according to claim 1, wherein the drug is administered orally or by injection.

* * * * *